United States Patent [19]

Hunt et al.

[11] Patent Number: 5,027,379
[45] Date of Patent: Jun. 25, 1991

[54] METHOD FOR IDENTIFYING DRILLING MUD FILTRATE INVASION OF A CORE SAMPLE FROM A SUBTERRANEAN FORMATION

[75] Inventors: Patricia K. Hunt, Solon; Bernard Zemel, Shaker Heights, both of Ohio

[73] Assignee: BP America Inc., Cleveland, Ohio

[21] Appl. No.: 483,232

[22] Filed: Feb. 22, 1990

[51] Int. Cl.$^5$ .................... A61B 6/80; G01N 23/223; C09K 7/00

[52] U.S. Cl. ........................ 378/4; 378/45; 378/51; 378/88; 250/255; 250/259; 175/42

[58] Field of Search .................... 250/255, 259; 378/4, 378/45, 49, 51, 53, 82, 88, 90; 175/42, 58

[56] References Cited

U.S. PATENT DOCUMENTS

| | | | |
|---|---|---|---|
| 4,540,882 | 9/1985 | Vinegar et al. | 250/255 |
| 4,571,491 | 2/1986 | Vinegar et al. | 378/207 |
| 4,583,242 | 4/1986 | Vinegar et al. | 378/20 |
| 4,613,754 | 9/1986 | Vinegar et al. | |
| 4,635,197 | 1/1987 | Vinegar et al. | 364/413.2 |
| 4,649,483 | 3/1987 | Dixon, Jr. | 364/422 |
| 4,663,711 | 5/1987 | Vinegar et al. | 364/420 |
| 4,688,238 | 8/1987 | Sprunt et al. | 378/4 |
| 4,710,946 | 12/1987 | Hinch et al. | 378/208 |
| 4,722,095 | 1/1988 | Muegge et al. | 378/4 |

OTHER PUBLICATIONS

Hunt et al., Computed Tomography as a Core Analysis Tool: Applications, Instrument Evaluation & Image Improvement Techniques, Journal of Petroleum Technology, Sep. 1988, 1203–1210.

Fransham, Displacement of Heavy Oil Visualized by CAT Scan, Journal of Canadian Petroleum Technology, May–Jun. 1987, pp. 42–47.

Vinegar et al., Tomographic Imaging of Three-Phase Flow Experiments, Rev. Sci. Instrum. 58 (1) Jan. 1987, pp. 96–107.

Wellington et al., CT Studies of Surfactant–Induced $CO_2$ Mobility Control, SPE 14393, Paper Prepared for Presentation at 60th Annual Tech. Conf. & Exhib. of Society of Petroleum Engrs., Las Vegas, NV, Sep. 22–25, 1985.

Sorbie et al., Miscible Displacements in Heterogeneous Core Systes: Tomographic Confirmation of Flow Mechanisms, SPE 18493, Paper Prepared for SPE International Symposium on Oilfield Chemistry in Houston, TX, Feb. 8–10, 1989.

Withjack et al., Computer Tomography Studies of 3-D Miscible Displacement Behavior in Laboratory Five-S-pot Model, SPF 18096, SPE 63rd Annual Technical Conference and Exhibition Held in Houston, TX, Oct. 2–5, 1988.

Wellington et al., X-Ray Computerized Tomography, Journal of Petroleum Technology, Aug. 1987, pp. 885–898.

Sedgwick et al., Application of X-Ray Imaging Techniques to Oil Sands Experiments, Journal of Canadian Petroleum Technology, Mar.–Apr. 1988, vol. 27, No. 2, pp. 104–110.

Vinegar, X-Ray CT and NMR Imaging of Rocks, Journal of Petroleum, Mar., 1986, pp. 257–259.

Primary Examiner—Edward P. Westin
Assistant Examiner—Don Wong

[57] ABSTRACT

A method of determining the invasion of drilling mud filtrate into a core sample from a borehole in a subterranean rock formation, comprising using a drilling mud which forms a filter cake during coring of the borehole thereby to limit invasion of drilling mud solids into the subterranean rock to an extent less than invasion of the base fluid in which the mud solids otherwise are normally suspended, dissolving a dopant in the base fluid of the drilling mud to form a solution having an X-ray attenuation characteristic different from the X-ray attenuation characteristic of the connate fluids in the subterranean formation, obtaining a core sample from the borehole using the doped drilling mud with the dopant remaining in solution in the base fluid under subterranean conditions at the core sample depth, scanning the core sample with a computed tomography scanner to determine the attenuation characteristics at a plurality of points in a cross-section in the core sample, and determining from the attenuation characteristics for the plurality of points the depth of invasion of the dopant-base fluid solution into the core sample.

17 Claims, 1 Drawing Sheet

METHOD FOR IDENTIFYING DRILLING MUD FILTRATE INVASION OF A CORE SAMPLE FROM A SUBTERRANEAN FORMATION

DISCLOSURE

The invention herein described relates generally to non-destructive analysis of mineral samples and, more particularly, to a new process for identifying drilling mud filtrate invasion of a core sample from a subterranean formation. A typical field for the application of this invention is in the sampling and testing of core samples from oil and gas wells. Although not limited to this use, the invention is hereinafter described with respect to this use.

BACKGROUND OF THE INVENTION

In drilling oil and gas wells, a conventional practice is to take samples of the strata through which the drill bit is passing. By analyzing these samples with respect to such parameters as permeability, porosity and fluid saturation, a great deal can be learned regarding the nature of the particular strata from which the sample was taken. These tests are generally included in the generic term "core analysis" which allows the characteristics of a particular reservoir to be evaluated.

When a well is drilled into a permeable formation, a drilling mud is circulated in the well to counterbalance the pressure of oil, gas, etc. A typical drilling mud consists of a base fluid of oil or water in which fine-grained mineral matter is suspended. The drilling mud may enter the formation and displace the connate fluids such as brine and hydrocarbons. The extent and nature of such drilling mud invasion is dependent upon various factors and generally is unpredictable. This is of particular consequence in the area of core sample analysis wherein various calculations, such as the calculation of native oil and water saturation, may be significantly affected by the amount of drilling mud invasion. These calculations may be made more accurately having knowledge that substantial amounts of drilling mud and/or drilling mud filtrate are present in the core sample.

Different methods of identifying drilling mud invasion of a core sample are known. Some of these methods involve the use of computed tomography (CT). Computed tomography is a technology that provides an image of the internal structure of a cross section or slice through an object via the reconstruction of a matrix of X-ray attenuation coefficients. Although the principles of tomography were discovered in the first half of this century, it has been only recently that the availability of computing power has made commercial applications practical. Computed tomography was introduced as a diagnostic X-ray technology for medical applications in 1971; and, more recently, it has been applied to materials analysis, especially in the area of non-destructive evaluation. For example, CT scanners have been used to examine fiber-reinforced organic matrix composites, die castings, engine components, and tensile specimens for manufacturing anomalies, absolute density, density gradients, porosity, and dimensional inspections. The technique also has been used to characterize two-phase fluid flow through pipes and through porous media including visualization of laboratory core floods. Additional core data that can be obtained includes oil saturation, porosity, and mineral distribution.

One method for determining drilling mud invasion using CT is disclosed by Vinegar et al in U.S. Pat. No. 4,540,882. According to this method, a first material is added to the drilling fluid, i.e., the drilling mud, to obtain a first fluid that has either an effective atomic number that is different from the effective atomic number of the connate fluids in the rock formation or a density that is different from the density of the connate fluids, or both. A preserved core sample is collected from the borehole for scanning by a computerized axial tomographic scanner to determine the attenuation coefficients at a plurality of points in a cross-section of the core sample. The preserved core sample is scanned with the scanner at first and second energies, and the determined attenuation coefficients for the plurality of points in the cross-section at each energy are used to determine an atomic number image for the cross-section of the core sample. The depth of invasion of the first fluid is then determined from the atomic number image, as an indication of the depth of invasion of the drilling fluid into the core sample.

Another method of identifying drilling mud invasion is disclosed by Muegge et al in U.S. Pat. No. 4,722,095. In this method, reliance is had upon the high CT attenuation coefficient of barite that is commonly employed as a weighting agent in drilling mud. Initially, mud filtrate is removed from the core sample, after which measurements are made of the pore volume, bulk volume and mud solid volume of the core sample using CT.

Both of the above described methods focus upon the invasion of the drilling mud into the core sample. Neither method, however, distinguishes between drilling mud invasion and drilling mud filtrate invasion. The extent of drilling mud filtrate invasion into the core sample is important to know because the filtrate, which could be oil or water, needs to be differentiated from formation fluids in laboratory fluid saturation tests if accurate reservoir saturations are to be determined.

When using a drilling mud which forms a poor filter cake at the surface of the core sample, such as a barite weighted mud, there can be sufficient barite present in the filtrate to determine the extent of filtrate invasion. However, it is more likely that any solid particles in the mud will be held up or filtered out by small pore throats further inside the core if not by those at the core perimeter and that only "pure" oil or water filtrate will reach the full invasion extent.

A more serious problem in detecting filtrate invasion arises when drilling muds which form good filter cakes are used, such as a calcium carbonate mud, as is desired to limit the extent of invasion by drilling mud solids into the core sample. With these drilling muds the solids thereof are more effectively filtered out of the base fluid which then invades the core sample to a greater depth than the drilling mud solids. The filtrate, i.e., the filtered base fluid which enters the core, will be solid-free water or oil and cannot be differentiated from the connate fluids in the rock formation using conventional oil and water saturation techniques.

Still other problems arise when using some of the dopants identified by Vinegar et al in U.S. Pat. No. 4,540,882. To give a drilling fluid an effective atomic number different from the effective atomic number of the connate fluids, Vinegar et al lists as exemplary additives barium sulfate, calcium carbonate, sodium tungstate and sodium iodide. No distinction is drawn between drilling mud invasion versus drilling mud filtrate invasion nor between the use of any of these four additives in conjunction with different types of drilling muds or different coring conditions such as those encountered in deep boreholes. For example, barium sulfate and calcium carbonate fail as a filtrate dopant because they are both insoluble and as solid particles would be filtered out of the filtrate at the core surface or partway into the core, but not to the full invasion extent. A problem with sodium tungstate is that many connate fluids in reservoir rock formations contain magnesium which would cause sodium tungstate to precipitate and then be filtered out of the base fluid along with the other drilling mud solids.

SUMMARY OF THE INVENTION

The present invention provides a novel method of determining the invasion of drilling mud filtrate into a core sample from a borehole in a subterranean rock formation. In carrying out the method, a drilling mud is used which forms a filter cake during coring of the borehole thereby to limit invasion of drilling mud solids into the subterranean rock to an extent less than invasion of the base fluid in which the mud solids otherwise are normally suspended. A dopant is dissolved in the base fluid of the drilling mud to form a solution having an X-ray attenuation characteristic (such as CT number) different from the X-ray attenuation characteristic of the connate fluids in the subterranean formation. A core sample from the borehole is obtained using the doped drilling mud with the dopant remaining in solution in the base fluid under subterranean conditions at the core sample depth. The core sample is scanned with a computed tomography scanner to determine the attenuation characteristic at a plurality of points in a cross-section in the core sample. The attenuation characteristics for the plurality of points are used to determine the depth of invasion of the dopant-base fluid solution into the core sample.

According to specific preferred embodiment, the dopant is first dissolved in the base fluid, particularly water, and then the base fluid is mixed with the mud solids to form the drilling mud. The dopant includes at least one iodide compound, more particularly an alkali metal iodide, and still more particularly potassium iodide for a water based drilling mud. The dopant is added to the mud in sufficient quantity to obtain a concentration of at least about 0.5%, more preferably at least 1%, and still more preferably between about 2% and about 4% by weight of the drilling mud.

The invention has particular application to core sampling at depths greater than about 9,000 feet. Preferably the drilling mud is of a type which provides for essentially complete filtering of the mud solids at the surface of the core sample. A drilling mud using calcium carbonate as a weighting agent in the drilling mud is desirable.

Upon determination of the extent of filtrate invasion, other core analysis procedures may be applied to the core sample such as connate fluid saturation measurements using a portion of the core sample identified as not invaded by the doped base fluid.

The foregoing and other features of the invention are hereinafter fully described and particularly pointed out in the claims, the following description and the annexed drawing setting forth in detail an illustrative embodiment of the invention, this being indicative, however, of but one of the various ways in which the principles of the invention may be employed.

DETAILED DESCRIPTION OF THE INVENTION

Figure 1:
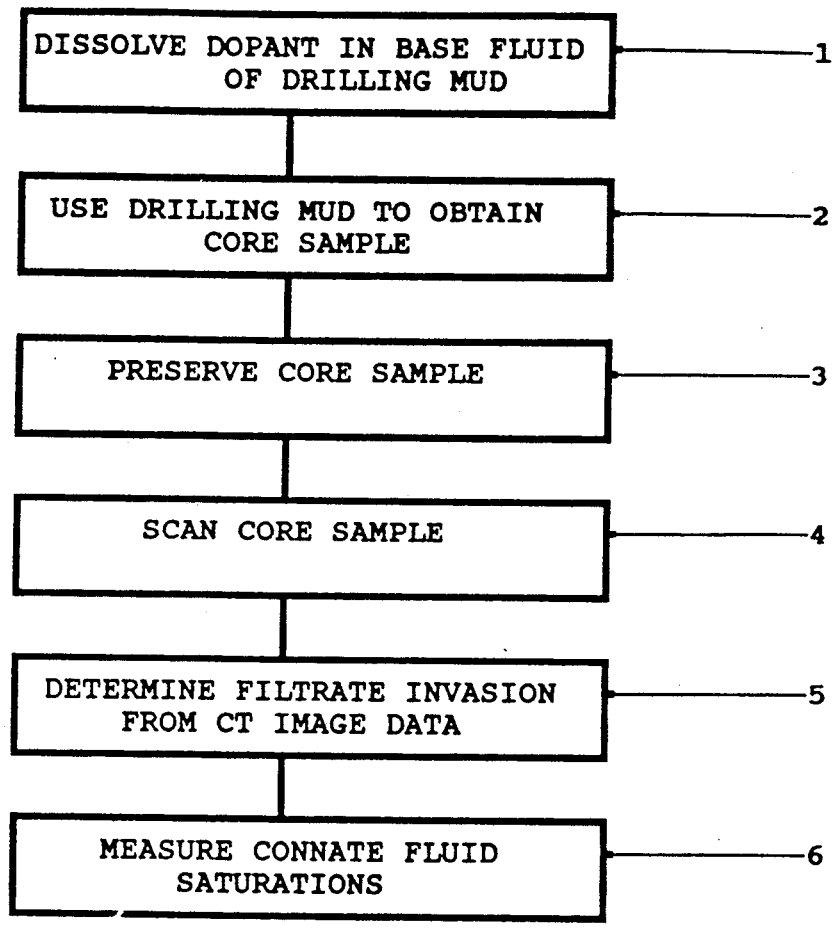
FIG. 1 is a flow chart depicting the steps involved in identifying drilling mud filtrate invasion of a core sample in accordance with the present invention.

A preferred procedure for carrying out the method of the present invention is depicted in FIG. 1. In step 1, a dopant is selected and added to a drilling mud mixture. Preferably, the dopant is added to the drilling mud mixture by first dissolving the dopant in the base fluid of the drilling mud mixture to form a solution and then the remaining solid components, or more simply "mud solids", are mixed with the solution to form the drilling mud mixture. As may be desired, the drilling mud mixture may be oil or water-based and consequently the base fluid will be either oil or water, respectively.

The dopant is added to the drilling mud mixture to give the solution made up of the base fluid and the dopant an X-ray attenuation characteristic different from the X-ray attenuation characteristic of the connate fluids so that the solution can be differentiated from the connate fluids by X-ray computed tomography. The X-ray attenuation characteristic may be the CT number which is a function of effective atomic number and density. Alternatively, the atomic number and density contributions to the CT number can be separated out such as by using dual energy CT scanning techniques to facilitate differentiation of compounds not discernible using single energy scanning.

In step two the drilling mud mixture containing the dopant in solution with the base fluid is used to drill a bore hole into a subterranean rock formation such as an oil or gas reservoir and, more particularly, to obtain rock core samples using conventional coring techniques. The drilling mud solids suspended in the solution of the base fluid and dopant will be partially or fully filtered out of the solution by small pore entries at or near the surface of the core sample. Any originally dissolved components in the drilling mud mixture that have come out of solution under conditions encountered by the drilling mud also will be partially or completely filtered out of the solution at or near the core surface. Some or all of these non-dissolved components will form a filter or mud cake at the outer surface of the core sample. Some of these non-dissolved components may enter the pores of the core, but will not invade the core to the same extent as the doped base fluid, i.e., the filtrate which may pass through the small pore throats and extend deeper into the core sample thereby displacing connate fluids. Preferably, a drilling mud mixture is selected that has excellent or good caking properties so that only the doped filtrate sans mud solids will invade the core sample while the mud solids are captured in a mud cake at the core surface.

Since analysis of the core sample will normally be conducted in a laboratory remote from the drilling site, the core sample obtained from the bore hole is preserved at step three. This is done to avoid loss of connate fluids from the core sample and further to prevent mixing or migrating of the dissolved dopant into the connate fluids contained in the core sample. The core sample may be preserved by conventional preservation and/or freezing techniques. An example of a preservation process is disclosed by Hunt et al in U.S. Pat. No. 4,505,161. In its preserved condition the core sample may be transported to the laboratory or other site for further analysis including CT scanning.

CT scanning of the core sample is carried out at step four to determine the extent of drilling mud filtrate invasion into the core sample. The CT scanner may be of conventional type such as that described by Vinegar et al in U.S. Pat. No. 4,540,882. This patent is hereby incorporated herein by reference for its description of a suitable computerized axial tomographic (CAT) scanner and sample positioning system that may be used in practicing the present invention. Operation of the system for core analysis may be facilitated by software available from the Shell Oil Company, Houston, Tex.

Preferably use is made of a procedure that eliminates "cupping" artifacts from the CT images generated by the scanner. The cupping artifacts, which result from the "beam hardening" phenomenon common in CT, will appear as a false, high X-ray attenuation ring at the perimeter of the image. This high X-ray attenuation ring cannot always be differentiated from a high X-ray attenuation ring around the perimeter that is caused by the presence of invaded doped filtrate. Consequently, the doped filtrate attenuation may be masked by the cupping artifacts. Various techniques for minimizing cupping effects are known, these including imaging through an aluminum core barrel, surrounding the object with media having attenuating properties close to the those of the object such as sand or a potassium iodide solution, and recalibrating the CT scanner using a material having CT attenuation similar to the object. Procedures for eliminating these cupping effects are disclosed in Hunt et al, "Calibrations for Analyzing Industrial Samples on Medical CT Scanners", Review of Progress in Quantitative Destructive Evaluation, Vol. 8A (Plenum Publishing Corporation, 1989), which is hereby incorporated herein by reference.

If desired an entire core interval may be scanned. However, the core interval, typically three or four inches in diameter, usually is of considerable length with 60 feet being a common length. Therefore, it normally will be more advantageous to scan selected segments of the core. The segments, i.e., disc-like sections of the core, preferably are selected from different lithologic zones along the core interval. The lithologic zones may be selected by eye or more preferably by using X-ray radiography. CT scanners often have a radiographic mode in which they may be operated to obtain radiographic images. From radiographic images of the entire core interval, different lithologic zones may be identified and located. From each lithologic zone, a few segments at representative locations may be chosen and scanned to obtain CT images.

The CT images are recorded, and the mud filtrate invasion is determined from the X-ray attenuation contrast created in the images by the presence of the doped base fluids. The recorded digital images are each composed of individual image units (pixels) arranged in a matrix. Computed tomography images consist of maps of linear X-ray attenuation coefficients within the object being imaged. Image pixels are assigned CT numbers in Hounsfield units.

The segments preferably are scanned by the CT scanner while still preserved. After being scanned, one or more representative segments from each lithology along the interval are removed from adjacent rock as by slicing a thin disc of rock corresponding to the segment. The segment or disc need only be thick enough to scan, i.e., have a thickness exceeding the CT scan slice thickness. The connate fluids and doped filtrate are then extracted from the disc using conventional chemical extraction techniques. A "base line scan" may then be obtained for each representative lithology by re-scanning the extracted disc preferably after resaturating with connate fluids. This base line scan can be used as a basis for comparison with other scans from that lithology.

The CT scan data is used at step 5 to determine filtrate invasion of the core segments. The CT images of the scanned segments may be used to provide a visual representation of drilling mud filtrate invasion, preferably after making base line corrections and any other appropriate corrections such as beam hardening corrections. The extent of filtrate invasion may also be accurately determined by comparing line profiles and dimensionally relating the line profile to the diameter of the core segment being imaged. A line profile is a profile of CT numbers (or equivalent parameter) across a diameter of the image. If proper beam hardening corrections have been applied, line profiles across the base line images will be relatively flat with the only variations present reflecting rock composition and rock porosity variations. The invaded rock images, however, will yield line profiles with edges indicating elevated X-ray attenuation due to the presence of the doped filtrate.

Figure 2:
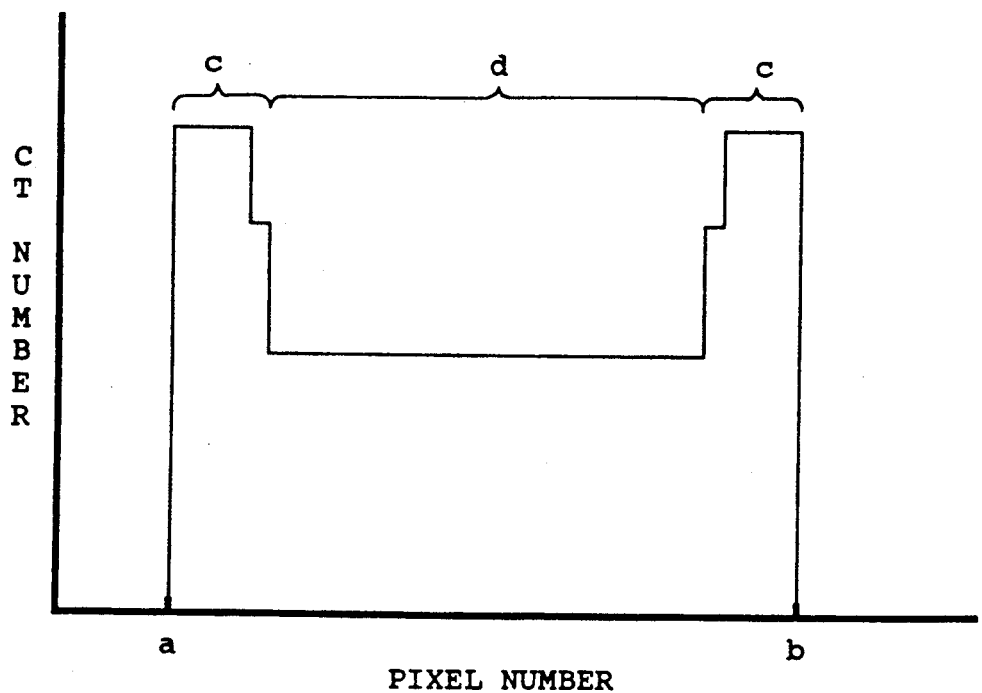
FIG. 2 is an exemplary line profile of CT numbers across a CT image of a four inch diameter core sample.

In FIG. 2 an exemplary line profile is shown. The line profile is taken across a diameter of a CT image with points "a" and "b" corresponding to diametrically opposed points on the perimeter of the core sample. As illustrated, the outer annular region denoted by brackets "c" has been invaded by the mud filtrate, i.e., the doped base fluid, which has a CT number higher than the connate fluids. The inner region denoted by bracket "d", however, is characterized by a much lower CT number indicating no filtrate invasion.

For cases in which the core rock is so permeable that the doped filtrate invaded the entire core, generally it will be necessary to resaturate the one or more cut discs from each lithology along the interval with connate fluids before base line scans are taken. In cases where it is determined that doped filtrate invasion occurred only part way into the core, resaturation of the extracted discs generally will not be necessary. Once the extent of filtrate invasion is known, uninvaded portions of the core rock may be identified for use in conducting more expensive, time-consuming and destructive tests to determine further characteristics of the core rock. Knowledge that the core is uninvaded by filtrate is important. For example, in determining relative percents of connate water versus oil, it is important to test rock with no base water or base oil from the drilling mud. Conventional techniques can be applied to the uninvaded portion of the rock to measure native water and/or oil saturations at step 6.

The CT image data may be analyzed in various ways. As above indicated, the line profiles from the images may be used to determine the extent of filtrate invasion. Alternatively, measurements may be taken from raw CT images or images of invaded versus extracted rock may be compared using, for example, 3D imaging equipment. Also, base line images may be subtracted from images of invaded rock on a pixel-by-pixel basis to obtain images showing filtrate invasion. These alternative methods are preferable for cases in which invasion is asymmetrical or nonconcentric with respect to the core perimeter.

For use in practicing the present invention, the dopant must remain in solution with the base fluid under downhole conditions encountered by the drilling mud so that it will be present in the filtrate to the full extent of filtrate invasion, which exceeds the extent of invasion by the mud solids. That is, the dopant must remain in solution at typically elevated temperatures and pressures at reservoir depth, or when in physical contact with reservoir rock, reservoir fluids and rock components that are potentially reactive, such as clays. The dopant preferably is anionic to avoid interaction with clays. Barite compounds generally are unsuitable because they are cationic and further may have a negative impact upon the mud if they are doubling as the weighting agent. Heavy metal compounds such as molybdates and tungstates are unsuitable because they will precipitate out of solution when in contact with calcium and magnesium ions commonly found in connate water in reservoir rock. For example, connate water from Prudhoe Bay includes sodium chloride, calcium chloride, $B_2O_3$, $MgCl_2$ and potassium chloride.

The solution made up of the base fluid and dopant must have an X-ray attenuation characteristic different from that of the connate reservoir fluids so that it can be differentiated from the connate fluids. Preferably, the difference is sufficient to enable differentiation by conventional single energy X-ray computed tomography. Alternatively, dual energy CT may be used to differentiate the doped base fluid from the connate fluids as by using differences in effective atomic number and/or density. In single energy CT, the units being compared are CT numbers or Hounsfield units. The CT number of the filtrate displacing oil and water in a 20% porosity sandstone should be approximately a few hundred units higher than the CT numbers of the displaced fluids. This requirement will vary as a function of CT scanner type, exact scanning parameters, and image analysis techniques. In dual energy CT, the effective atomic number and density contributions to the CT number can be separated thereby facilitating differentiation of compounds not discernible using single energy.

As a further criteria for selection of the dopant, the dopant in the quantity added should not adversely affect drilling mud performance. For example, the dopant should not adversely affect drilling mud properties such as viscosity and weight, or at least there should be the ability to alter the drilling mud mixture to compensate for any adverse effects caused by the dopant. In general, the dopant should be effective at concentrations of no more than a few percent by weight of the mud mixture, as higher concentrations could alter mud properties. The dopant concentration should be no greater than 10% by weight, preferably no greater than 5% by weight and more preferably no greater than 4% by weight.

A preferred dopant for water-based drilling muds is potassium iodide (KI). Potassium iodide preferably is added to the drilling mud in sufficient quantity to obtain a concentration of at least 0.5% by weight of the drilling mud mixture and more preferably at least 1% by weight and still more preferably between 2 to 4% by weight of the drilling mud mixture. Potassium iodide is useful in shallow wells and in deep well applications wherein core samples are taken at depths exceeding 8,000 feet and, more particularly, depths between 9,000 and 13,000 feet, or greater.

The dopant may also be selected from other iodide compounds including combinations thereof. Sodium iodide (NaI) is slightly more effective than potassium iodide as a dopant so that a lesser concentration may be used, but sodium iodide is more costly. The concentration of sodium iodide may be as low as 0.4% by weight of the drilling mud mixture although preferably sodium iodide, as well as the other iodide compounds alone or in combination, is added to obtain a concentration at least 1% by weight and more preferably from about 2% to about 4% by weight.

The iodide compounds, particularly potassium iodide and sodium iodide, are particularly useful with calcium carbonate drilling muds as well as other water based drilling muds which form good filter cakes. Other dopants include, for example, akali metal halides and more particularly akali metal iodides. Still other dopants are chromide compounds such as potassium dichromate and manganese compounds such as potassium permanganates. Such dopants would be added in a concentration sufficient to differentiate the doped filtrate from connate fluids.

A preferred mud is a bland mud with a calcium carbonate weighting agent. Although the use of a high X-ray attenuation barite weighting agent would enhance CT visualization, the calcium carbonate weighting agent is preferable due to its superior fluid loss control properties. The CT number of the filtrate which results from use of an undoped bland calcium carbonate mud is very similar to that of the fluids it displaces (oil and connate water) and, therefore, the presence of the filtrate will be not apparent without addition of a dopant such as potassium iodide.

Procedures for enhancing CT data thereby permitting use of a lesser concentration of dopant include increasing precision by lengthening scan times and thereby increasing number of incident X-ray photons, increasing precision and accuracy by using known techniques to eliminate beam hardening and resultant data artifacts, and increasing precision by taking multiple scans of each slice and adding them together in the data manipulation step.

The use of CT dopants at the well site may be facilitated, for example, by providing a slug or pill of doped mud to be used only during coring instead of doping the entire mud system.

Principles of the invention can have application to other nondestructive imaging technologies that presently are known, such as nuclear magnetic resonance (NMR) and possibly others developed in the future. The dopant selected necessarily would impart a physical characteristic to the dopant-base fluid solution that enables differentiation from the connate fluids by the scanning technology being employed. In the case of NMR, this would be a magnetic resonance characteristic different from the magnetic resonance characteristic of the connate fluid, such difference being sufficient to permit differentiation between the doped base fluid filtrate and the connate fluids.

Although the invention has been shown and described with respect to a preferred embodiment, equivalent alterations and modifications will occur to others skilled in the art upon the reading and understanding of this specification. The present invention includes all such equivalent alterations and modifications and is limited only by the scope of the following claims.

What is claimed is:

1. A method of determining the invasion of drilling mud filtrate into a core sample from a borehole in a subterranean rock formation, the method comprising:

using a drilling mud which forms a filter cake during coring of the borehole thereby to limit invasion of drilling mud solids into the subterranean rock to an extent less than invasion of the base fluid in which the mud solids otherwise are normally suspended;

dissolving a dopant in the base fluid of the drilling mud to form a solution having an X-ray attenuation characteristic different from the X-ray attenuation characteristic of the connate fluids in the subterranean formation;

obtaining a core sample from the borehole using the doped drilling mud with the dopant remaining in solution in the base fluid under subterranean conditions at the core sample depth;

scanning the core sample with a computed tomography scanner to determine the attenuation characteristic at a plurality of points in a cross-section in the core sample; and determining from the attenuation characteristics for the plurality of points the depth of invasion of the dopant-base fluid solution into the core sample.

2. A method as set forth in claim 1, wherein said dissolving step includes first dissolving the dopant in the base fluid and then mixing the base fluid with the mud solids to form the drilling mud.

3. A method as set forth in claim 1, wherein the dopant includes at least one iodide compound.

4. A method as set forth in claim, 3, wherein said at least one iodide compound is an alkali metal iodide, or an iodide compound soluble in the base fluid.

5. A method as set forth in claim 1, wherein said alkali metal iodide is potassium iodide.

6. A method as set forth in claim 1, wherein the dopant is added to the mud in sufficient quantity to obtain a concentration of at least about 1% by weight of the drilling mud.

7. A method as set forth in claim 6, wherein the dopant is added to the mud in sufficient quantity to obtain a concentration of between about 2% and about 4% by weight of the drilling mud.

8. A method as set forth in claim 1, wherein the core sample depth is greater than about 8,000 feet.

9. A method as set forth in claim 8, wherein the core sample depth is greater than about 9,000 feet.

10. A method as set forth in claim 1, wherein the drilling mud is of a type which provides for essentially complete filtering of the mud solid at the surface of the core sample.

11. A method as set forth in claim 1, said using step includes using calcium carbonate as a weighting agent in the drilling mud.

12. A method as set forth in claim 11, wherein the dopant includes at least one iodide compound.

13. A method as set forth in claim 12, wherein said at least one iodide compound has a concentration of 0.5% to 5% by weight of the drilling mud.

14. A method as set forth in claim 1, wherein the dopant is anionic.

15. A method as set forth in claim 1, further comprising the step of measuring connate fluid saturation using a portion of the core sample identified as not invaded by the dopant-base fluid.

16. A method as set forth in claim 1, wherein said obtaining step includes preserving the core sample to minimize loss of connate fluids from the core sample and to minimize mixing or migrating of the dissolved dopant into the connate fluids.

17. A method as set forth in claim 1, including the step of obtaining a base line scan of the core sample after the dopant has been extracted from the core sample.

* * * * *